(12) United States Patent
Nebolon et al.

(10) Patent No.: US 11,330,798 B2
(45) Date of Patent: May 17, 2022

(54) RFID TAG INSERTION CARTRIDGE AND AN RFID TAG INSERTION TOOL

(71) Applicant: Somark Group Pty Ltd, Sydney (AU)

(72) Inventors: Joe Nebolon, San Diego, CA (US);
Steve Elliott, San Diego, CA (US);
Paul Donohoe, Warlingham (GB);
Adrian Knight, Sydney (AU)

(73) Assignee: Somark Group Limited, Sydney (AU)

( * ) Notice: Subject to any disclaimer, the term of this patent is extended or adjusted under 35 U.S.C. 154(b) by 0 days.

(21) Appl. No.: 16/755,329

(22) PCT Filed: Oct. 12, 2018

(86) PCT No.: PCT/AU2018/051109
§ 371 (c)(1),
(2) Date: Apr. 10, 2020

(87) PCT Pub. No.: WO2019/071320
PCT Pub. Date: Apr. 18, 2019

(65) Prior Publication Data
US 2020/0296926 A1 Sep. 24, 2020

Related U.S. Application Data

(60) Provisional application No. 62/571,762, filed on Oct. 12, 2017.

(51) Int. Cl.
*G08B 13/14* (2006.01)
*A01K 11/00* (2006.01)
(Continued)

(52) U.S. Cl.
CPC .............. *A01K 11/006* (2013.01); *A61D 7/00* (2013.01); *G06K 19/07758* (2013.01);
(Continued)

(58) Field of Classification Search
CPC ........ A01K 11/006; G08B 13/14; A61D 7/00; G06K 19/07758; A61B 90/39; A61B 2090/3987; A61B 90/98
(Continued)

(56) References Cited

U.S. PATENT DOCUMENTS 3,658,061 A    4/1972  Hall
4,223,674 A *  9/1980  Fluent ............... A61M 37/0069
                                                 604/507

(Continued)

FOREIGN PATENT DOCUMENTS

AU    2018200814 B2    3/2018
AU    2017218461 A1    9/2018
(Continued)

OTHER PUBLICATIONS

Webpage, "Revolyzer: Voluntary Running Assay," preclinics, 1 page.

(Continued)

*Primary Examiner* — Tai T Nguyen
(74) *Attorney, Agent, or Firm* — Patterson Thuente Pedersen, P.A.

(57) ABSTRACT

Disclosed herein is an RFID tag insertion cartridge comprising a hollow needle in which an RFID tag is disposed. The cartridge comprises an optional housing in the form of a shell that is shown transparently. The cartridge comprises a carriage that is movably mounted and to which the hollow needle is attached for withdrawing the needle. Also disclosed herein is a RFID tag insertion tool.

7 Claims, 5 Drawing Sheets

(51) Int. Cl.
*A61D 7/00* (2006.01)
*G06K 19/077* (2006.01)
*A61B 90/00* (2016.01)
*A61B 90/98* (2016.01)

(52) U.S. Cl.
CPC .............. *A61B 90/39* (2016.02); *A61B 90/98* (2016.02); *A61B 2090/3987* (2016.02)

(58) Field of Classification Search
USPC .......... 340/572.1, 572.7; 604/116, 117, 218, 604/272, 506
See application file for complete search history.

(56) References Cited

U.S. PATENT DOCUMENTS

| | | | |
|---|---|---|---|
| 4,262,632 A | 4/1981 | Hanton et al. | |
| 4,392,493 A | 7/1983 | Niemeijer | |
| 4,440,078 A | 4/1984 | McCrery, Jr. et al. | |
| 4,671,277 A | 6/1987 | Beuchat | |
| 4,950,249 A | 8/1990 | Jagger et al. | |
| 5,024,727 A | 6/1991 | Campbell et al. | |
| 5,053,774 A | 10/1991 | Schuermann et al. | |
| 5,074,318 A | 12/1991 | Campbell et al. | |
| 5,151,089 A | 9/1992 | Kirk, III et al. | |
| 5,211,129 A * | 5/1993 | Taylor .............. | G06K 19/07758 119/215 |
| 5,232,455 A | 8/1993 | Hollister | |
| 5,250,026 A * | 10/1993 | Ehrlich .............. | A61M 37/0069 604/117 |
| 5,288,291 A * | 2/1994 | Teoh ................. | A61M 37/0069 604/218 |
| 5,551,319 A | 9/1996 | Spaulding et al. | |
| 5,632,732 A | 5/1997 | Szabo et al. | |
| 5,673,647 A | 10/1997 | Pratt | |
| 5,709,662 A | 1/1998 | Olive et al. | |
| 5,816,197 A | 10/1998 | DeStefano et al. | |
| D405,882 S | 2/1999 | Yale | |
| 6,013,122 A | 1/2000 | Klitzman et al. | |
| 6,033,421 A | 3/2000 | Theiss et al. | |
| 6,115,636 A | 9/2000 | Ryan | |
| 6,186,144 B1 | 2/2001 | Davis et al. | |
| 6,263,762 B1 | 7/2001 | Zeitler | |
| 6,345,553 B1 | 2/2002 | Adler et al. | |
| 6,616,638 B2 | 9/2003 | Peters, III | |
| 6,695,819 B2 | 2/2004 | Kobayashi | |
| 6,719,737 B2 | 4/2004 | Kobayashi | |
| 6,901,885 B1 | 6/2005 | Kleinsasser | |
| 7,098,394 B2 | 8/2006 | Armer et al. | |
| 7,230,539 B2 | 6/2007 | Klein | |
| 7,553,293 B2 | 6/2009 | Jensen et al. | |
| D609,804 S | 2/2010 | Uchida et al. | |
| 8,353,917 B2 | 1/2013 | Mandecki et al. | |
| 8,502,670 B2 | 8/2013 | Cha et al. | |
| 9,418,321 B1 | 8/2016 | Gruda et al. | |
| 10,349,630 B2 | 7/2019 | Florczak | |
| 10,645,905 B2 | 5/2020 | Gandola et al. | |
| D899,594 S | 10/2020 | Wang | |
| D902,402 S | 11/2020 | Wang | |
| 2002/0020646 A1 | 2/2002 | Groth et al. | |
| 2002/0154065 A1 | 10/2002 | Mejia et al. | |
| 2003/0062988 A1 | 4/2003 | Mandecki et al. | |
| 2004/0097780 A1 * | 5/2004 | Otsuka .............. | A61M 37/0069 600/7 |
| 2004/0131234 A1 | 7/2004 | Long et al. | |
| 2004/0144333 A1 | 7/2004 | Finlayson | |
| 2004/0220527 A1 | 11/2004 | Buckley et al. | |
| 2004/0244341 A1 | 12/2004 | Kurt | |
| 2004/0246126 A1 | 12/2004 | Pitts | |
| 2004/0260270 A1 | 12/2004 | Cohen | |
| 2005/0051109 A1 | 3/2005 | Fantin et al. | |
| 2005/0234475 A1 * | 10/2005 | Cordes ................. | A01K 11/006 606/117 |
| 2006/0071782 A1 | 4/2006 | Ahmed et al. | |
| 2006/0071785 A1 | 4/2006 | Ahmed et al. | |
| 2006/0177649 A1 | 8/2006 | Clark et al. | |
| 2007/0103314 A1 | 5/2007 | Giessler | |
| 2007/0272157 A1 | 11/2007 | Giessler | |
| 2007/0288249 A1 | 12/2007 | Rowe et al. | |
| 2008/0008357 A1 | 1/2008 | Barreto Martins | |
| 2008/0036356 A1 | 2/2008 | Ward et al. | |
| 2008/0036846 A1 | 2/2008 | Hopkins et al. | |
| 2008/0042849 A1 | 2/2008 | Saito et al. | |
| 2008/0065181 A1 | 3/2008 | Stevenson | |
| 2008/0106419 A1 | 5/2008 | Sakama et al. | |
| 2008/0143619 A1 | 6/2008 | Wotherspoon | |
| 2008/0158432 A1 | 7/2008 | Hwang et al. | |
| 2008/0168948 A1 | 7/2008 | Truitt et al. | |
| 2008/0221549 A1 | 9/2008 | Cohen | |
| 2008/0247637 A1 | 10/2008 | Gildenberg | |
| 2008/0306437 A1 | 12/2008 | Jacobson et al. | |
| 2008/0314325 A1 | 12/2008 | Hempstead et al. | |
| 2009/0062748 A1 | 3/2009 | Moller et al. | |
| 2009/0153304 A1 | 6/2009 | Sands et al. | |
| 2009/0182267 A1 * | 7/2009 | Painchaud ........ | A61M 37/0069 604/60 |
| 2009/0209903 A1 | 8/2009 | Cherif-Cheikh et al. | |
| 2009/0241857 A1 | 10/2009 | Zolfaghari | |
| 2009/0273439 A1 | 11/2009 | Selsor | |
| 2009/0292246 A1 | 11/2009 | Slate et al. | |
| 2009/0311295 A1 | 12/2009 | Mathiowitz et al. | |
| 2010/0023021 A1 | 1/2010 | Flaherty | |
| 2010/0160809 A1 | 6/2010 | Laurence et al. | |
| 2010/0222767 A1 * | 9/2010 | Gluck ................. | A61M 5/3273 604/506 |
| 2010/0295682 A1 | 11/2010 | August et al. | |
| 2010/0295687 A1 | 11/2010 | Kuzniar et al. | |
| 2011/0077659 A1 | 3/2011 | Mandecki et al. | |
| 2011/0304505 A1 | 12/2011 | Parker et al. | |
| 2011/0316693 A1 | 12/2011 | Loen | |
| 2012/0016315 A1 | 1/2012 | Radmer et al. | |
| 2012/0086620 A1 | 4/2012 | Johnson | |
| 2012/0126948 A1 | 5/2012 | Brunski | |
| 2012/0193415 A1 | 8/2012 | Coiro, Sr. et al. | |
| 2012/0215230 A1 * | 8/2012 | Lubock ................. | A61B 90/39 606/116 |
| 2012/0226288 A1 | 9/2012 | Mays et al. | |
| 2013/0046174 A1 * | 2/2013 | Fischell ................ | A61B 90/39 600/431 |
| 2013/0267962 A1 | 10/2013 | Michelson | |
| 2014/0055248 A1 | 2/2014 | Hammelbacher | |
| 2014/0128880 A1 | 5/2014 | Gandola et al. | |
| 2014/0204400 A1 | 7/2014 | Budleski | |
| 2015/0004679 A1 | 1/2015 | Conger et al. | |
| 2015/0032060 A1 | 1/2015 | Patel | |
| 2015/0217059 A1 | 8/2015 | Ashby et al. | |
| 2015/0269798 A1 | 9/2015 | Small | |
| 2016/0037749 A1 | 2/2016 | Gandola et al. | |
| 2017/0124264 A1 | 5/2017 | Jordan et al. | |
| 2018/0017679 A1 | 1/2018 | Valouch et al. | |
| 2018/0242899 A1 | 8/2018 | Oddsson et al. | |
| 2019/0053465 A1 | 2/2019 | Knight et al. | |
| 2019/0391002 A1 | 12/2019 | Knih | |
| 2020/0045932 A1 | 2/2020 | Knight et al. | |
| 2020/0060229 A1 | 2/2020 | Knight et al. | |
| 2020/0404882 A1 | 12/2020 | Gandola et al. | |

FOREIGN PATENT DOCUMENTS

| | | |
|---|---|---|
| CN | 2602591 Y | 2/2004 |
| CN | 1547430 A | 11/2004 |
| CN | 101057561 A | 10/2007 |
| EP | 0300110 A2 | 1/1989 |
| EP | 0364044 A1 | 4/1990 |
| EP | 1911347 A1 | 4/2008 |
| EP | 2840890 A1 | 3/2015 |
| EP | 2967000 A1 | 1/2016 |
| EP | 3413704 A1 | 12/2018 |
| EP | 3694595 A1 | 8/2020 |
| GB | 2468587 A | 9/2010 |
| JP | H05-317278 A | 12/1993 |
| JP | 2009-069108 A | 4/2009 |
| JP | 3152587 U | 8/2009 |

(56) References Cited

FOREIGN PATENT DOCUMENTS

| | | |
|---|---|---|
| JP | 2009-232786 A | 10/2009 |
| JP | 2010-266289 A | 11/2010 |
| JP | 2013-503641 A | 2/2013 |
| JP | 6376570 B2 | 8/2018 |
| KR | 20090058746 A | 6/2009 |
| KR | 10-1940275 B1 | 1/2019 |
| SG | 11201507292 | 10/2015 |
| SG | 10201707223 | 10/2017 |
| WO | WO 1998/041084 A1 | 9/1998 |
| WO | WO 2002/082892 A2 | 10/2002 |
| WO | WO 2007/033407 A1 | 3/2007 |
| WO | WO 2011/028926 A2 | 3/2011 |
| WO | WO 2013/163339 A1 | 10/2013 |
| WO | WO 2014/151852 A1 | 9/2014 |
| WO | WO 2015/005802 A1 | 1/2015 |
| WO | WO 2016/113554 A1 | 7/2016 |
| WO | WO 2017/093453 A1 | 6/2017 |
| WO | WO 2017/131337 A1 | 8/2017 |
| WO | WO 2017/136898 A1 | 8/2017 |
| WO | WO 2017/136900 A1 | 8/2017 |
| WO | WO 2019/071317 A1 | 4/2019 |
| WO | WO 2019/071320 A1 | 4/2019 |
| WO | WO 2019/071321 A1 | 4/2019 |
| WO | WO 2020/220043 A1 | 10/2020 |

OTHER PUBLICATIONS

Mainetti, "An RFID-Based Smart Cage for Animal Behavior Analysis," Smart 2014: The Third International Conference on Smart Systems, 2014, 6 pages.

PCT/AU2018/051109 Search Report and Written Opinion dated Dec. 20, 2018, 16 pages.

Application and File history for U.S. Appl. No. 29/701,974, filed Aug. 15, 2019. Inventors: Bates et al.

Application and File history for U.S. Appl. No. 16/755,316, filed Apr. 10, 2020. Inventors: Knight et al.

Application and File history for U.S. Appl. No. 16/077,729, filed Aug. 13, 2018. Inventors: Knight et al.

Application and File history for U.S. Appl. No. 16/871,491, filed May 11, 2020. Inventors: Gandola et al.

Application and File history for U.S. Appl. No. 14/778,489, filed Sep. 18, 2015. Inventors: Gandola et al.

"Mysensalab" available Aug. 29, 2020, [online], [site visited Aug. 29, 2020]. Retrieved from Internet, URL: https://mysensalab.com/products/ (Year: 2020).

EP Patent Application No. 18867114.3, Extended EP Search Report dated Jun. 2, 2021, 7 pages.

\* cited by examiner

RFID TAG INSERTION CARTRIDGE AND AN RFID TAG INSERTION TOOL

CROSS-REFERENCE TO RELATED APPLICATIONS

The present application claims the benefit of U.S. Provisional Application No. 62/571,762, filed Oct. 12, 2017, and PCT International Application No.: PCT/AU2018/051109, filed Oct. 12, 2018, both of which are entitled, "AN RFID TAG INSERTION CARTRIDGE AND AN RFID TAG INSERTION TOOL", and both of which are hereby incorporated herein in their entirety by reference.

TECHNICAL FIELD

The disclosure herein generally relates to an RFID tag insertion cartridge and an RFID tag insertion tool.

BACKGROUND

Radio frequency identification ("RFID") tags can be implanted in an animal for identifying the animal, for example. The procedure to implant the RFID tag may require two highly skilled persons and can take many minutes to complete. An easier way to implant RFID tags that can be performed by less skilled persons quickly and safely is desirable.

SUMMARY

Disclosed hererin is an RFID tag insertion cartridge. The RFID tag insertion cartridge comprises a hollow needle in which an RFID tag is disposed. The RFID tag insertion cartridge comprises a carriage that is movably mounted and to which the hollow needle is attached for withdrawing the needle. The RFID tag insertion cartridge comprises a stop pin disposed in the hollow needle for stopping an inward movement of the RFID tag when the needle is withdrawn and so eject the RFID tag.

An embodiment comprises a fitting for removable attachment to an RFID tag insertion tool operable to move the carriage. The fitting may be configured for uniquely orientating the RFID insertion cartridge with respect to the RFID tag insertion tool when attached thereto. The fitting may comprise at least one of a plurality of different diameter radial pins and a plurality of different width slots for receiving the plurality of different diameter radial pins. The fitting may comprise a bayonet fitting.

In an embodiment, an end of the stop pin is for abutting the RFID tag. Another end of the stop pin may comprise a hook.

In an embodiment, the carriage comprises a proximal end configured to be engagingly received by a distal end of the fitting for retaining the needle within the housing when so withdrawn.

An embodiment comprises a housing comprising a linear bearing surface in contact with a plurality of protruding linear bearing pads of the carriage.

Disclosed herein is an RFID tag insertion tool. The RFID tag insertion tool comprises an actuator that is user operable and a transmission assembly operationally coupled to the actuator. The transmission assembly comprises a coupler configured to couple to an RFID insertion cartridge and when so coupled transmit movement of the actuator to a needle of the RFID tag insertion cartridge. The RFID tag insertion tool comprises a biasing element arranged to inwardly bias the coupler.

In an embodiment, the transmission assembly comprises a displacement multiplier. The displacement multiplier may comprise a pinion arranged to move with the actuator. The displacement multiplier comprises a fixed rack and a translatably mounted rack that meshes with the pinion.

An embodiment comprises a housing in which the fixed rack is fixed.

An embodiment comprises a user releasable catch for outwardly retaining the coupling.

An embodiment comprises a fitting for removable attachment of the RFID tag insertion tool. The fitting may be configured for uniquely orientating the RFID insertion cartridge with respect to the RFID tag insertion tool when attached thereto. The fitting may comprise at least one of a plurality of different diameter radial pins and a plurality of different width slots for receiving the plurality of different diameter radial pins. The fitting may comprise a bayonet fitting.

Any of the various features of each of the above disclosures, and of the various features of the embodiments described below, can be combined as suitable and desired.

BRIEF DESCRIPTION OF THE FIGURES

Embodiments will now be described by way of example only with reference to the accompanying figures in which.

DESCRIPTION OF EMBODIMENTS

Figure 1:
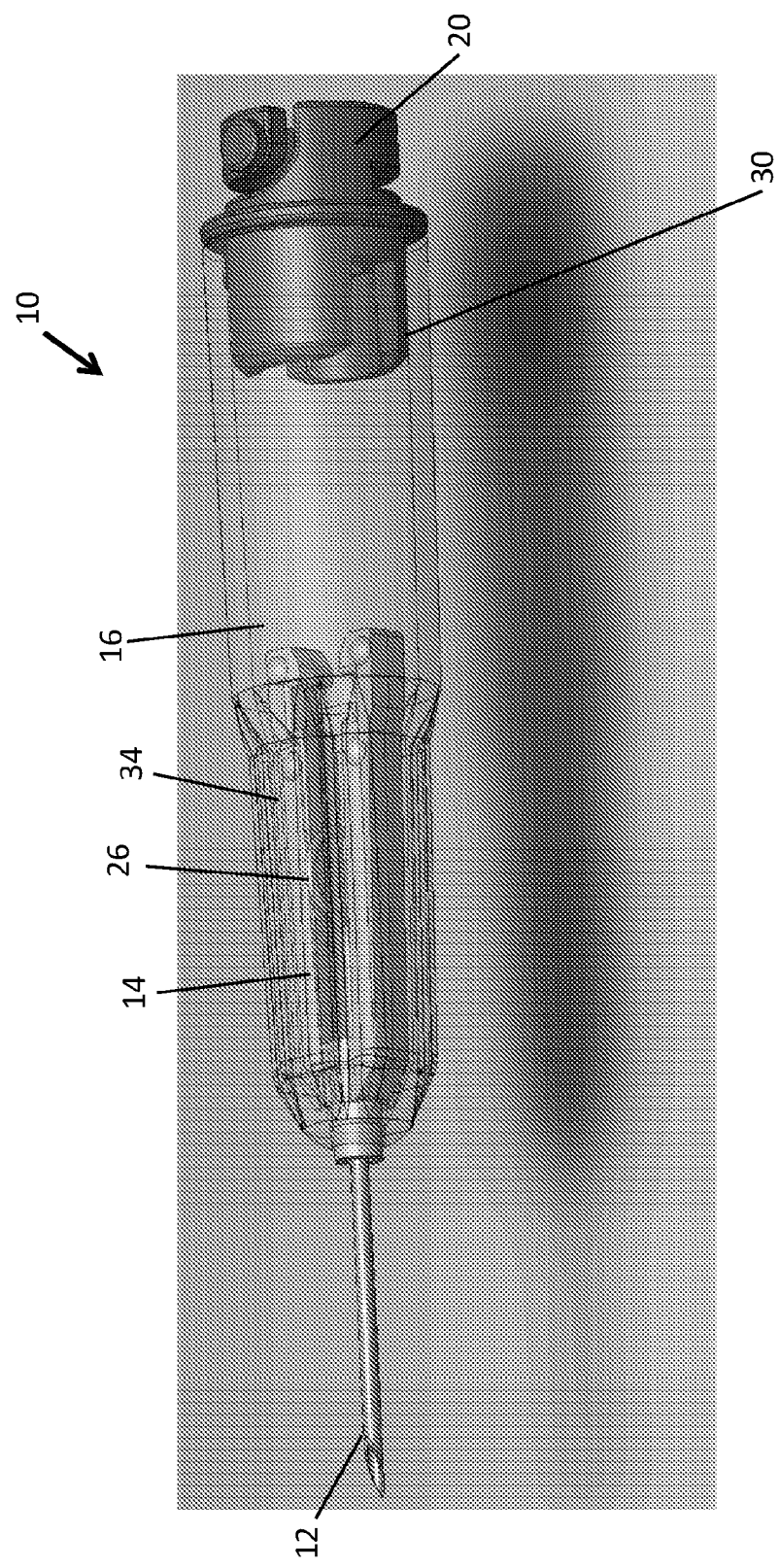
FIG. 1 shows a perspective view of an embodiment of an RFID tag insertion cartridge.
Figure 2:
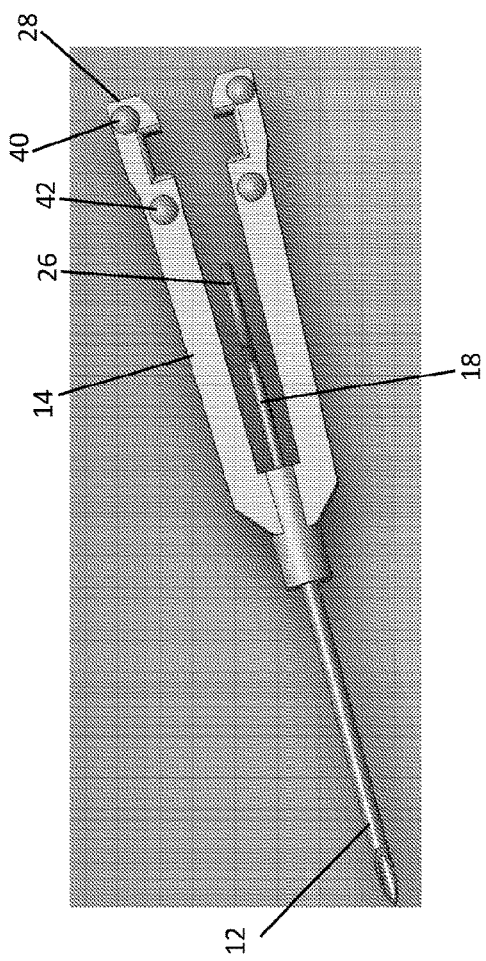
FIG. 2 shows a top view of a carriage of the RFID tag insertion cartridge of FIG. 1 and needle attached thereto.

FIG. 1 shows a perspective view of an embodiment of an RFID tag insertion cartridge ("cartridge") generally indicated by the numeral 10. The cartridge 10 comprises a hollow needle 12 in which an RFID tag is disposed (and so hidden from view). The cartridge 10 comprises an optional housing 16 in the form of a shell that is shown transparently. The cartridge 10 comprises a carriage 14 that is movably mounted and to which the hollow needle 12 is attached for withdrawing the needle. FIG. 2 shows a top view of the carriage 14 and needle 12 attached thereto. The cartridge 10 comprises a stop pin 18 disposed in the hollow needle 12 for stopping an inward movement of the RFID tag when the needle 12 is withdrawn and so eject the RFID tag.

Figure 3:
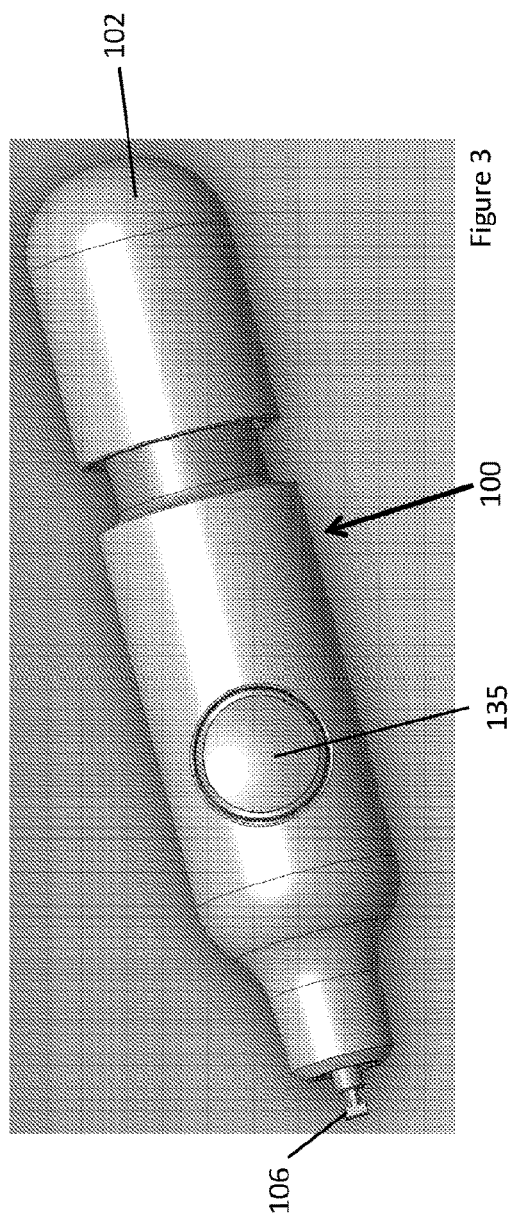
FIG. 3 shows a perspective view of an embodiment of an RFID tag insertion tool.
Figure 4:
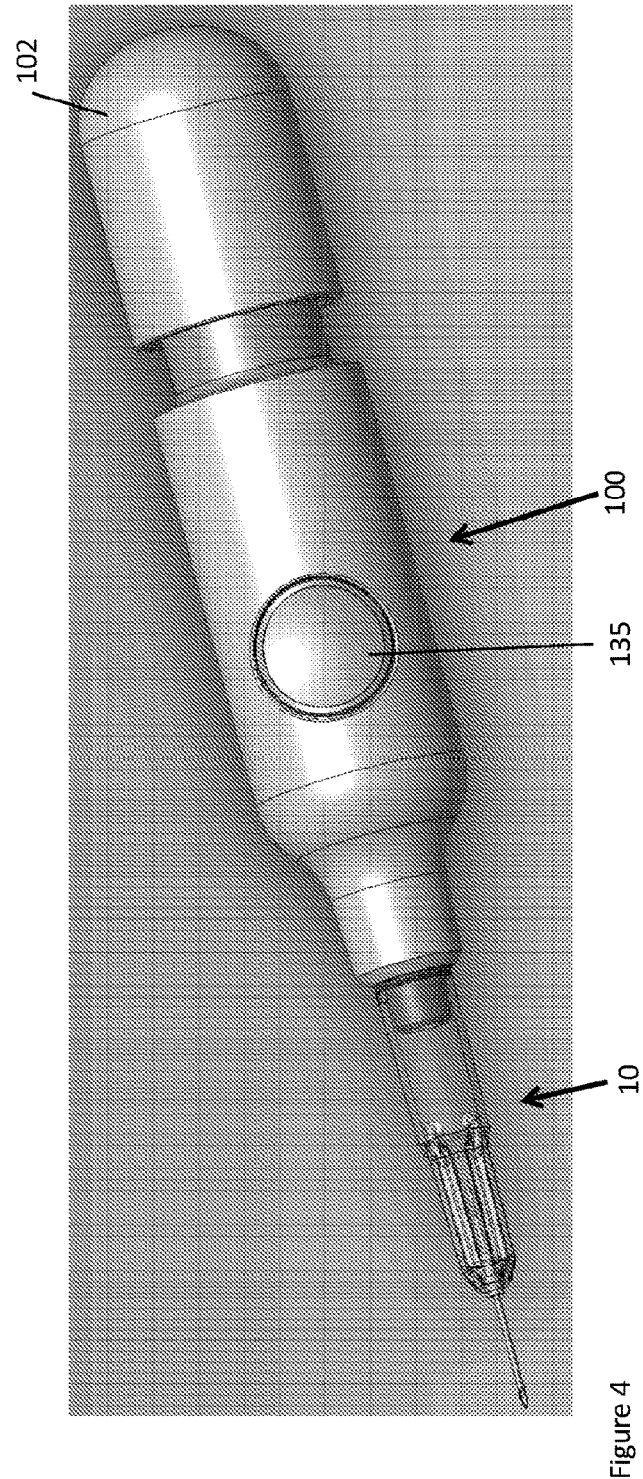
FIG. 4 shows a perspective view of the RFID tag insertion cartridge of FIG. 1 attached to the RFID tag insertion tool of FIG. 3.

The RFID tag insertion cartridge 10 comprising a fitting 20 for removable attachment to an RFID tag insertion tool operable to move the carriage 14. FIG. 3 shows a perspective view of an embodiment of an RFID tag insertion tool 100. FIG. 4 shows a perspective view of the RFID tag insertion cartridge 10 attached to the RFID tag insertion tool 100.

Figure 7:
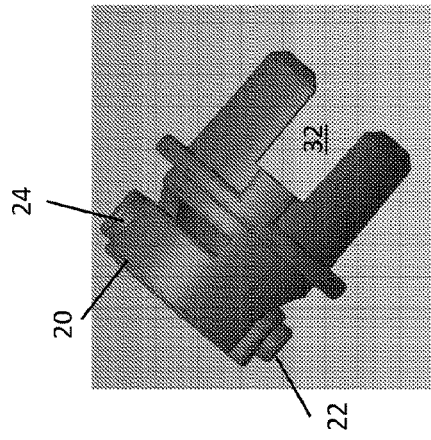
FIGS. 5, 6 and 7 respectively show an end-on view, a perspective view and a side view of a fitting of the RFID tag insertion cartridge.
Figure 6:
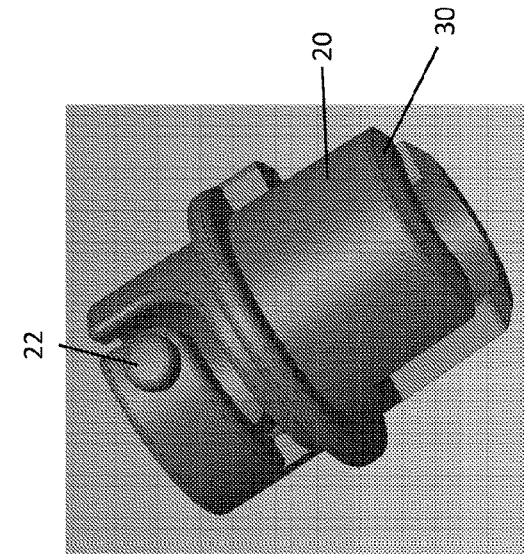
Figure 5:
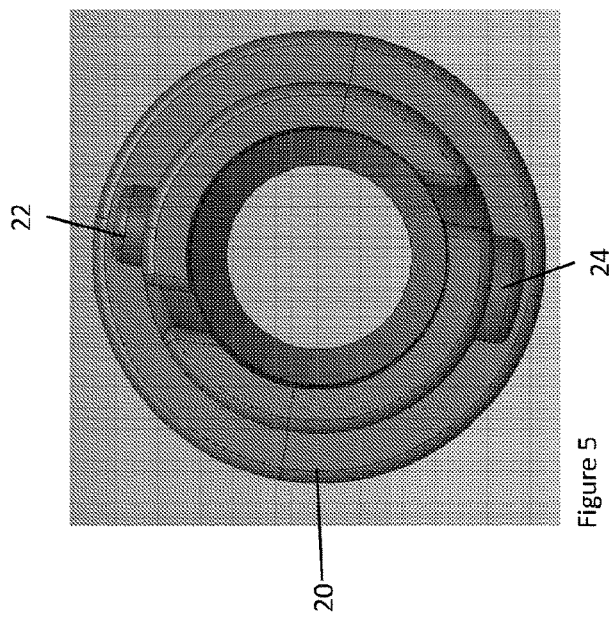

FIGS. 5, 6 and 7 respectively show an end-on view, a perspective view and a side view of the fitting 20. The fitting 20 is configured for uniquely orientating the RFID insertion cartridge 10 with respect to the RFID tag insertion tool 100 when attached thereto. The fitting 20 comprises a plurality of different diameter radial pins 22,24 that are received by a plurality of different width slots defined by the RFID insertion tools 100. In an alternative embodiment, the fitting 20 defines the slots and the RFID insertion tool comprises the radial pins. The fitting 2—comprises a bayonet fitting, but in alternative embodiment may comprise a screw fitting or generally any suitable form of fitting.

An end of the stop pin 18 is disposed in the hollow needle 12 (and so hidden) for abutting the RFID tag therein. Another end 26 of the stop pin 18 comprises a hook.

The carriage 14 comprises a proximal end 28 configured to be engagingly received by the distal end 30 of the fitting 20 for retaining the needle 12 within the shell when so withdrawn. The proximal end 28 is received into at least one slot 32 defined by the fitting 20. When so received, a friction fit between the proximal end 28 of the carriage 14 and the distal end of the fitting 20 holds the needle to the fitting. The proximal end 28 of the carriage 14 comprises at least one, and in this embodiment a plurality of friction elements 38 in the form of side-wall engaging protrusions 40,42 for the frictional fit.

In this but not all embodiments, the housing 12 comprises a linear bearing surface 34 in contact with the carriage 14. In an alternative embodiment, the housing may be replaced with a cage or framework with the linear bearing. In yet another embodiment, the linear bearing surface 34 may be replaced with a roller bearing, or generally any suitable form of bearing.

Figure 8:
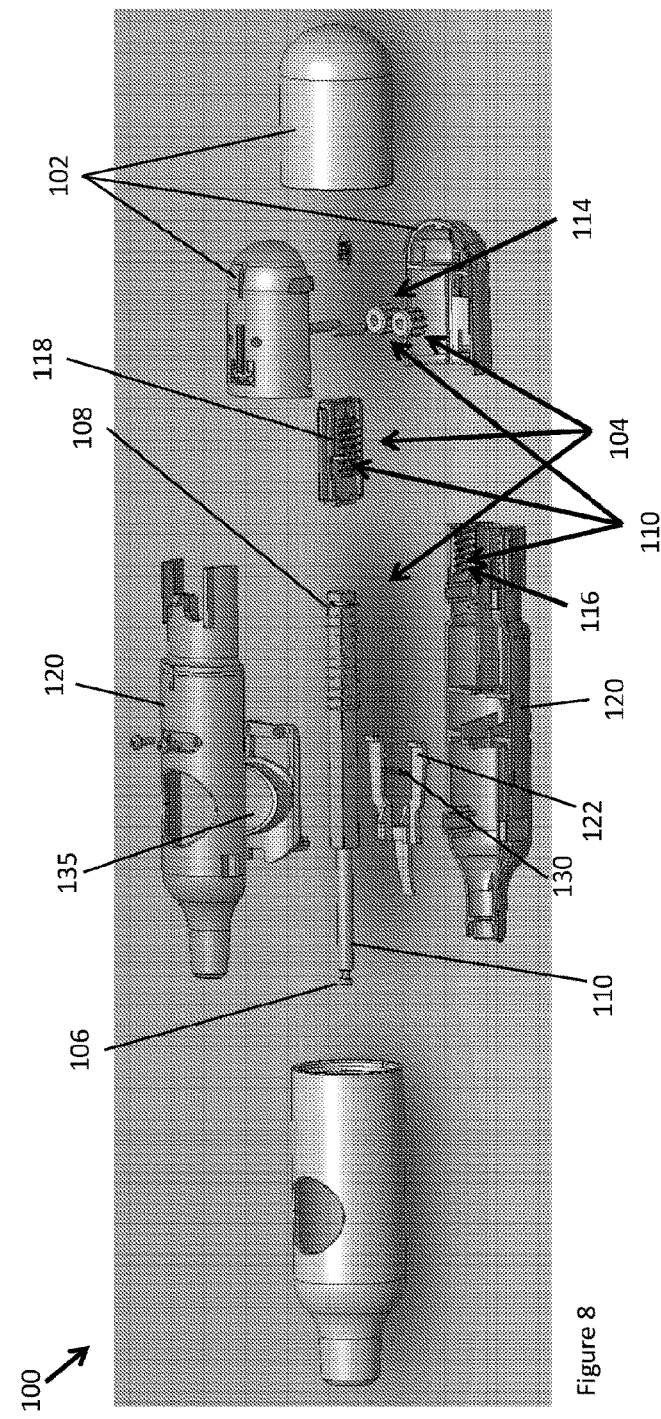
FIG. 8 shows an exploded perspective view of the RFID tag insertion tool of FIG. 3.

FIG. 8 shows an exploded perspective view of the RFID tag insertion tool 100 ("the tool"). The tool 100 is, in this embodiment, in the form of a handheld RFID tag insertion tool 100, however it may not be handheld in an alternative embodiment. The tool may be configured to sit on a bench, for example. The tool 100 comprises an actuator 102 in the form of a button that can be inwardly depressed by a user. The tool 100 comprises a transmission assembly 104 operationally coupled to the actuator 102. The transmission 100 assembly comprising a coupler 106 configured to couple to the carriage 14 of the RFID insertion cartridge 10 and when so coupled transmit movement of the actuator 102 to the needle 12 of the RFID tag insertion cartridge 10. The tool 100 comprises a biasing element 108 in the form of a compression spring 108 arranged to inwardly bias the coupler 106. The coupler 106 is attached to an end of a shaft 110. The shaft is disposed within the compression spring 108. One end of the compression spring 108 contacts a circlip 124 attached to the shaft 110. Another end of the compression spring contacts a spring seat 126 in the form of a housing bulkhead attached to the interior of the housing 120.

Figure 9:
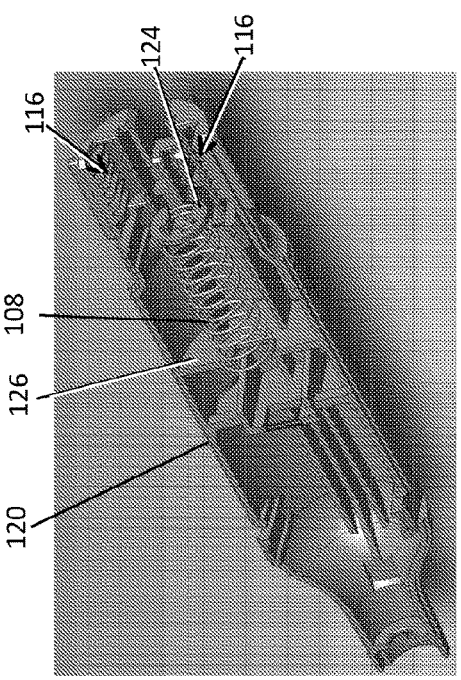
FIG. 9 shows a portion of a housing of the RFID tag insertion tool of FIG. 3.

The transmission assembly 104 comprises a displacement multiplier 110 in the form of a displacement doubler 110. The displacement multiplier 110 comprises a translatably mounted pinion 104 operationally coupled to the actuator 102 (in this embodiment attached to by way of an axle attached to the actuator 102 and around which the pinion rotates). The translatably mounted pinion 114 meshes with a fixed rack 116 best seen in FIG. 9 and a translatably mounted rack that abuts the shaft, however in an alternative embodiment the translatable mounted rack is attached to the shaft. The fixed rack is a rack fixed to a housing 120 of the tool 100. A linear displacement of the actuator 102 results in twice the linear displacement of the coupler 106. The rack and pinion arrangement described can be cascaded to further multiply the displacement of the coupling 106 with respect of the actuator 102. Generally, any suitable form of multiplier, for example a pulley system or gear box, may be used.

Figure 10:
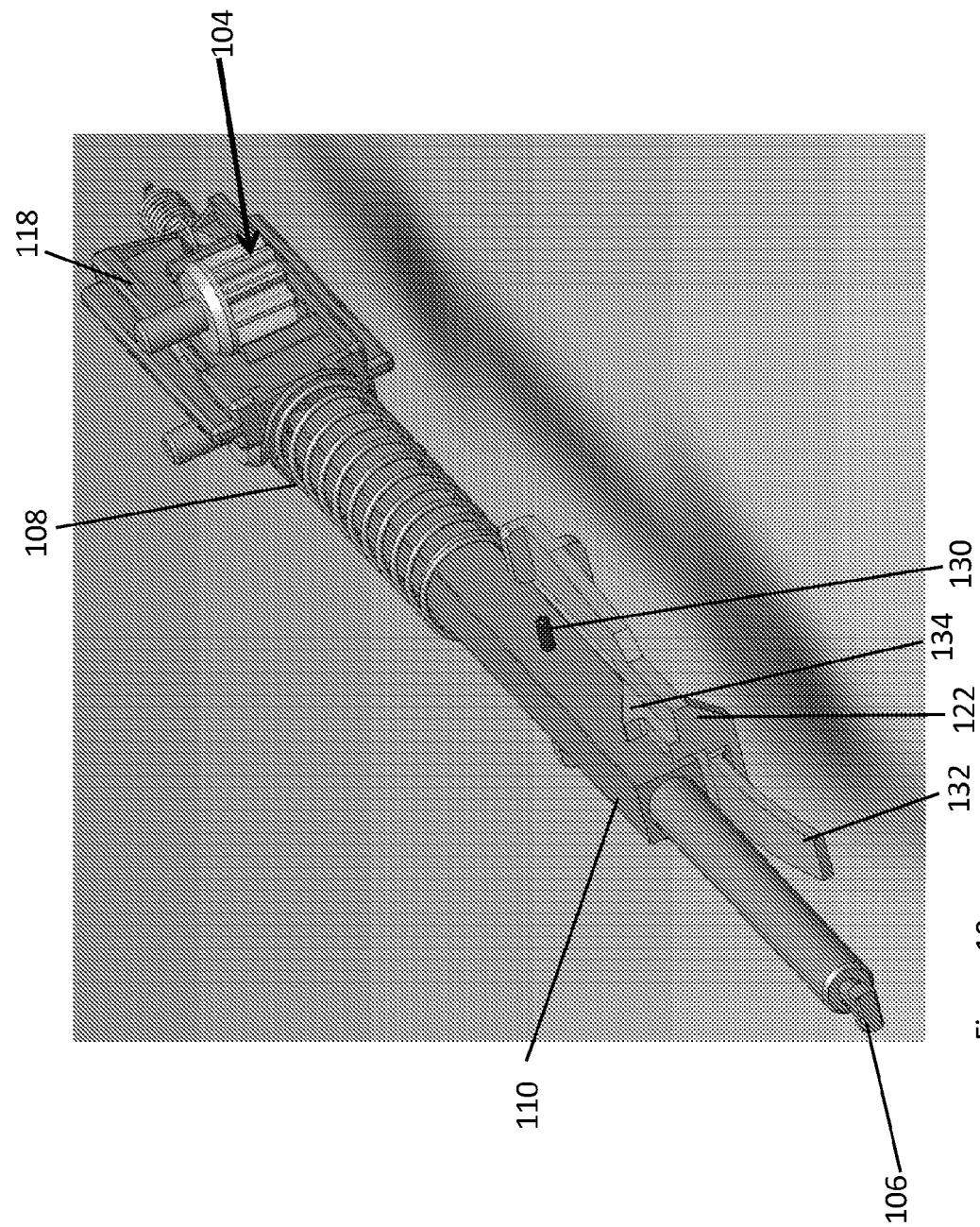
FIG. 10 shows a mechanism of the tool of FIG. 3.

FIG. 10 shows a mechanism of the tool 100. The tool 100 comprises a user releasable catch 122 for outwardly retaining the coupling. The catch 122 is biased towards the shaft 110 by a biasing element 132 in the form of a leaf spring. A pin 130 extending outwardly from the shaft 110 is arranged to ride over a ramp 134 and catch behind a back face thereof. A user depressing a button 135 operationally coupled to the ramp is operated by the user to move the catch 122 away from the shaft 110 and release the pin 130. The compression spring 108 is then able to move the shaft 110 and coupler 106 inwardly which in turn withdraws the needle 12.

In use, the user attaches the cartridge 10 to the tool 100 and operates the actuator 102 in the form of the button by moving it inwardly until the catch 122 catches on the pin 130. The user then inserts the needle 12 into an animal. The user then releases the catch 122 by pressing button 134 resulting in the withdrawal of the needle into the housing 16 and so deposit the RFID tag. The needle 12 is then withdrawn leaving the RFID tag within the animal.

Figure 11:
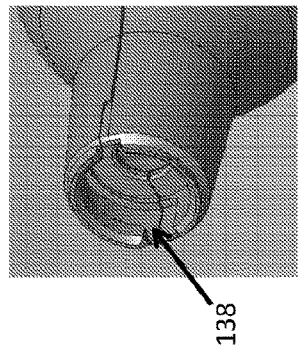
FIG. 11 shows an end perspective view of the housing of the RFID tag insertion tool of FIG. 3.

FIG. 11 shows an end perspective view of the housing 120 of the RFID tag insertion tool 100, showing a fitting 138 for removable attachment of the RFID tag insertion tool, comprising circumferential slots for receiving the pins 22,24 of the cartridge 10. The fitting 138 is configured for uniquely orientating the RFID insertion cartridge 10 with respect to the RFID tag insertion tool 100 when attached thereto. The fitting 138 comprises a plurality of different width slots for receiving the plurality of different diameter radial pins. The fitting 138 comprises a bayonet fitting.

Variations and/or modifications may be made to the embodiments described without departing from the spirit or ambit of the invention. The present embodiments are, therefore, to be considered in all respects as illustrative and not restrictive. Reference to a feature disclosed herein does not mean that all embodiments must include the feature.

Prior art, if any, described herein is not to be taken as an admission that the prior art forms part of the common general knowledge in any jurisdiction.

In the claims which follow and in the preceding description of the invention, except where the context requires otherwise due to express language or necessary implication, the word "comprise" or variations such as "comprises" or "comprising" is used in an inclusive sense, that is to specify the presence of the stated features but not to preclude the presence or addition of further features in various embodiments of the invention.

The invention claimed is:

1. An RFID tag insertion cartridge for use with an RFID tag insertion tool, the RFID tag insertion cartridge comprising:
   a hollow needle in which an RFID tag is disposed;
   a carriage attached to the hollow needle that is configured to be movably mounted to withdraw the needle;
   a fitting that is configured for removable attachment to the RFID tag insertion tool that is operable to move the carriage, the fitting uniquely orientating the RFID insertion cartridge with respect to the RFID tag insertion tool when attached thereto, wherein the fitting comprises at least one of a plurality of different diameter radial pins and a plurality of different width slots for receiving the plurality of different diameter radial pins; and a stop pin disposed in the hollow needle and configured to stop an inward movement of the RFID tag when the needle is withdrawn and thereby eject the RFID tag.

2. An RFID tag insertion cartridge for use with an RFID tag insertion tool, the RFID tag insertion cartridge comprising:

a hollow needle in which an RFID tag is disposed;

a carriage attached to the hollow needle that is configured to be movably mounted to withdraw the needle, the carriage including a bayonet fitting configured for removable attachment to the RFID tag insertion tool that is operable to move the carriage; and a stop pin disposed in the hollow needle and configured to stop an inward movement of the RFID tag when the needle is withdrawn and thereby eject the RFID tag.

3. An RFID tag insertion cartridge for use with an RFID tag insertion tool, the RFID tag insertion cartridge comprising:

a hollow needle in which an RFID tag is disposed;

a carriage attached to the hollow needle that is configured to be movably mounted to withdraw the needle;

a fitting configured for removable attachment of the carriage to the RFID tag insertion tool that is operable to move the carriage;

a stop pin disposed in the hollow needle and configured to stop an inward movement of the RFID tag when the needle is withdrawn and thereby eject the RFID tag; and a housing comprising a linear bearing surface in contact with a plurality of protruding linear bearing pads of the carriage, wherein the carriage comprises a proximal end configured to be engagingly received by a distal end of the fitting to retain the needle within the housing when so withdrawn.

4. An RFID tag insertion cartridge for use with an RFID tag insertion tool, the RFID tag insertion cartridge comprising:

a hollow needle in which an RFID tag is disposed;

a carriage attached to the hollow needle that is configured to be movably mounted to withdraw the needle;

a bayonet fitting configured for removable attachment of the carriage to the RFID tag insertion tool that is operable to move the carriage, the bayonet fitting uniquely orientating the RFID insertion cartridge with respect to the RFID tag insertion tool when attached thereto;

a stop pin disposed in the hollow needle and configured to stop an inward movement of the RFID tag when the needle is withdrawn and thereby eject the RFID tag; and a housing comprising a linear bearing surface in contact with a plurality of protruding linear bearing pads of the carriage, wherein the carriage comprises a proximal end configured to be engagingly received by a distal end of the fitting to retain the needle within the housing when so withdrawn.

5. The RFID tag insertion cartridge defined by claim 4 wherein the bayonet fitting comprises at least one of a plurality of different diameter radial pins and a plurality of different width slots for receiving the plurality of different diameter radial pins.

6. The RFID tag insertion cartridge defined by claim 4 wherein an end of the stop pin is for abutting the RFID tag.

7. The RFID tag insertion cartridge defined by claim 6 wherein another end of the stop pin comprises a hook.

* * * * *